United States Patent
Schaub et al.

(10) Patent No.: US 6,835,760 B2
(45) Date of Patent: Dec. 28, 2004

(54) USE MIXTURES AS IMPRESSION OR DOUBLING COMPOSITIONS IN THE DENTAL AREA

(75) Inventors: Matthias Schaub, Düsseldorf (DE); Michael Freckmann, Köln (DE); Holger Urbas, Krefeld (DE)

(73) Assignee: Heraues Kulzer GmbH & Co. KG, Hanau (DE)

( * ) Notice: Subject to any disclaimer, the term of this patent is extended or adjusted under 35 U.S.C. 154(b) by 398 days.

(21) Appl. No.: 10/054,211

(22) Filed: Jan. 22, 2002

(65) Prior Publication Data

US 2002/0156149 A1 Oct. 24, 2002

(30) Foreign Application Priority Data

Jan. 29, 2001 (DE) .......................... 101 04 079

(51) Int. Cl.⁷ .............................. A61K 6/10; A61C 5/00
(52) U.S. Cl. ...................... 523/109; 528/28; 433/228.1
(58) Field of Search .......................... 523/109; 528/28; 433/228.1

(56) References Cited

U.S. PATENT DOCUMENTS 5,118,290 A  *  6/1992  Muller et al. .................. 433/48
5,739,245 A  *  4/1998  Lubbers et al. ............... 528/28

FOREIGN PATENT DOCUMENTS

| DE | 44 39 769 A1 | 5/1996 |
| DE | 199 42 467 A1 | 4/2001 |
| EP | 0 269 819 B1 | 6/1988 |
| EP | 0 939 107 A2 | 9/1999 |

* cited by examiner

Primary Examiner—Tae H. Yoon
(74) Attorney, Agent, or Firm—Norris McLaughlin & Marcus PA

(57) ABSTRACT

A dental impression or doubling composition comprising alkoxysilyl-functional polyethers, having 20–95% polyether groups, 0.2 to 25% $SiR^1R^2R^3$ groups and 0–10% urethane or urea groups, and a mixture comprising water and organic or inorganic acids, or both.

6 Claims, No Drawings

USE MIXTURES AS IMPRESSION OR DOUBLING COMPOSITIONS IN THE DENTAL AREA

The invention relates to the use of mixtures as impression or doubling compositions in the dental area.

Impression compositions, which are used in the dental area, are known (cf. R. G. Craig, Restorative Dental Materials, The C. V. Moosbe-Comp. St. Louis, Toronto, London, 1980, page 1979 ff). Such materials must satisfy high requirements.
1. Pleasant odor and taste and an esthetic appearance.
2. The compositions may not contain any toxic or irritating components.
3. The compositions must have a shelf life of several months.
4. It must be possible to produce the compositions economically and the impression must be precise.
5. The compositions must be easily handled.
6. The curing characteristics must correspond to clinical requirements.
7. The cured compositions must be elastic and, when stressed in tension, must not be deformed permanently.
8. The cured compositions must have a sufficient compressive strength and must not break.
9. At room temperature and normal humidity, the cured compositions must be dimensionally stable until, after an appropriate time, accurate plaster impressions can be prepared.
10. The cured compositions must not cause any damage to the plaster and must be compatible with other impression compositions.

The impression compositions, which are based on alkoxysilyl-functionalized polyethers, are described in EP 0 269 819 B1.

The use of mixtures is disclosed there, which contain
A) a polyaddition product, containing ether, urethane, and urea groups and terminal alkoxysilane groups, with a predominantly linear molecular structure, exclusively aliphatic or cycloaliphatic bound ether, urethane and urea segments, with an average molecular weight Mn of 800–2000, characterized by the
   a) a 25 to 90 percent by weight content of polyether groups,
   b) a 0.5 to 10 percent by weight content of urethane groups (—NH—CO—O—),
   c) a 0.5 to 10 percent by weight content of urea groups (—NH—CO—NH—) and
   d) terminal groups having the formula —NR—$(CH_2)_n$—$SiR_1R_2R_3$,
      in which n represents the numbers 1 to 6,
      R represents hydrogen or —$(CH_2)_n$—$SiR_1R_2R_3$,
      $R_1R_2R_3$ independently of one another represent C1 to C4 alkoxy, the terminal —$SiR_1R_2R_3$ alkoxysilyl group content being 1 to 25 percent by weight and
B) a mixture containing water and organic and/or inorganic acids in a ratio by weight of 1:0.01 to 1:40 as impression or doubling compositions in the dental area.

However, these systems do not fulfill all of the requirements, mentioned above, to the desired extent.

These impression compositions must be synthesized especially by expensive, multi-step methods. Moreover, these products are highly viscous, since diisocyanates are reacted with dihydroxypolyethers, so that there necessarily is an increase in the average molecular weight (Mn) and, with that, also an increase in viscosity. With that, the possibilities of formulating pasty compositions with the polyaddition products, known from the art, is greatly limited, since either high diluent contents or low filler contents must be selected in order to obtain compositions, which can be processed and therefore are not too viscous.

Finally, the impression compositions based on the polyaddition product described in EP 0 269 819 B1, when mixed with water and acid, have unfavorable curing kinetics, which are characterized by a short processing time and, at the same time, by a long setting time.

In the DE 44 39 769, synthetic products are disclosed with a polyaddition product, containing at least one silane, ether and urethane group, with a predominantly linear molecular structure with aliphatic or cycloaliphatic, bound ether or urethane segments and a number average molecular weight ranging from 800 to 20,000, the polyaddition product having the following distinguishing features:
a) a polyether group content of 20 to 90 and especially of 50 to 80 parts by weight, based on 100 parts by weight of polyaddition product,
b) a content of urethane groups of Formula I $$—NH—CO—O \qquad (I)$$

of 0.5 to 10 and especially of 1 to 8 parts by weight, based on 100 parts by weight of polyaddition product,
c) as well as a content of terminal alkoxysilyl groups of Formula II $$—NR—(CH_2)_m—SiR^1R^2R^3 \qquad (II)$$

in which
m is a number ranging from 1 to 6 and especially 3,
R is hydrogen or a group of Formula (III)

$$—(CH_2)_m—Si\ R^1R^2R^3 \qquad (III)$$

in which m, $R^1$, $R^2$ and $R^3$ have the meanings given and at least one of the groups $R^1$, $R^2$ and $R^3$ is a group of Formula IV $$—(O—C_pH_{2p})_q—O—R^4 \qquad (IV)$$

in which
p is a number from 2 to 4 and especially 3 and
q represents a number of from 1 to 100 and especially 2 to 4 and
$R^4$ represents an alkyl, aralkyl, vinyl, vinylcarbonyl, α-methylvinylcarbonyl or β-methylvinylcarbonyl group,
in which the remaining $R^1$, $R^2$ and $R^3$ groups represent methyl, ethyl or $C_1$ to $C_4$ alkoxy, insofar as they are not groups defined above,
and the synthetic materials furthermore contain at least one catalyst for the condensation of the silane groups.

An expensive, multi-step synthesis methods, which requires a transesterification step of commercially obtainable silanes with compounds having the structure H—(O—$C_pH_{2p})_q$—O—$R^4$ is also a disadvantage of this system. The high toxic potential of the groups of the general formula H—(O—$C_pH_{2p})_q$—$OR^4$ is a further disadvantage of this system.

It is an object of the present invention to avoid the disadvantages of the known impression compositions based on alkoxysilyl-functional polyethers, that is, especially to make available impression compositions based on commercially obtainable or easily synthesized (preferably in one step), low viscosity (viscosity<50 Pas) alkoxysilyl-functional polyethers, which are distinguished by advantageous setting kinetics (that is, processing times of 2 to 3 minutes and curing times of less than 4 minutes), that is, by a so-called snap-set behavior (slow induction time of up to several minutes and, subsequently, very rapid setting).

Pursuant to the invention, this objective is accomplished by a use described in claim 1.

It is a question here of the use of mixtures containing
A) alkoxysilyl-functional polyethers with linear or branched main chains with an average molecular weight (Mn) of 800 to 20,000, containing 20 to 95 percent of polyether groups and
0.2 to 25 percent of $SiR^1R^2R^3$ alkoxysilyl groups, in which $R^1$, $R^2$ and $R^3$, independently of one another, are hydrogen, alkyl or alkoxy, and
0 to 10 percent of urethane groups or 0 to 10 percent of urea groups, and
B) a mixture, containing water and organic and/or inorganic acids in a ratio by weight of 1:0.01 to 1:40,
as impression or doubling composition in the dental area.
In further embodiments of the invention
2. mixtures are used, the component A) of which has a branched main chain;
3. mixtures are used, the component A) of which is free of urethane groups;
4. mixtures are used, the component A) of which has an average molecular weight of 1500 to 15,000;
5. mixtures are used, the component A) of which contains 2 to 15 percent of $SiR^1R^2R^3$ alkylsilane groups.

Some of the alkoxysilyl-functional polyethers, which are used pursuant to the invention, such as the MS polymer of the Kanaka Corporation, are commercially available. These are polypropylene oxide derivatives, which are functionalized with methyldimethoxysilyl groups (such as MS Polymer S303H).

Furthermore, polyethers, which are used pursuant to the invention, can be synthesized in that linear or branched polyether polyols or linear or branched, amino-terminal polyethers are reacted with suitably functionalized alkoxysilanes and optionally with polyisocyanates at temperatures of 20° to 150° C. The use of a catalyst may be necessary for this reaction.

Suitable for the preparation of the inventive alkoxysilyl-functional polyethers are, for example, polyether polyols, which are known from the production of polyurethanes (for example, Ullmann's Encyclopedia of Industrial Chemistry, vol. 21, pp. 665 to 717, VCH Publishers Inc., 1992 or U.S. Pat. No. 5,672,652). These are compounds, which are synthesized by the polymerization of epoxides such as ethylene oxide, propylene oxide, butylene oxide, tetrahydrofuran, styrene oxide or epichlorohydrin with themselves in the presence, for example, of $BF_3$, or by the addition reaction of these epoxides, optionally in admixture or consecutively, to starter components with reactive hydrogen atoms, such as alcohols, glycols, glycerin, trimethylolpropane, pentaerythritol, sugars, ethylenediamine, diethylenetriamine, etc. Frequently, those polyethers are preferred, which predominantly (up to 90 percent of the OH groups present in the polyether) have primary hydroxy groups. The polyethers, which are synthesized by the so-called DMC catalysis, for example, with zinc hexacyanocobaltate (U.S. Pat. No. 3,278,457), have especially proven their value. In a preferred embodiment, the polyether polyols used have a molecular weight (Mn) of 1000 to about 15,000 and are distinguished by a hydroxy function not the of about 1.5 to 4.

Furthermore suitable for the synthesis of the inventive alkoxysilyl-functional polyethers are so-called amino-terminated polyethers, which are also known from the production of polyurethanes. The amino-terminated polyethers are obtained starting from polyether polyols by exchanging the hydroxy groups for ammonia or primary amines (for example, U.S. Pat. No. 3,847,992). For the synthesis of the amino-terminated polyethers, the polyether polyols, listed above, can be used in principle as starting materials. In a preferred embodiment, the amino-terminated polyethers used have a molecular weight (Mn) of about 500 to about 15,000 and an amino functionality of about 2 to 4.

Suitable functionalized alkoxysilanes for the synthesis of the inventive alkoxysilyl-functionalized polyethers are distinguished by the following structure:

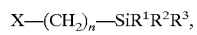

$$X-(CH_2)_n-SiR^1R^2R^3,$$

In which X represents a group capable of reacting with a hydroxy or amino group n represents a number from 1 to 8, and $R^1$, $R^2$ and $R^3$ independently of one another represent hydrogen, alkyl or alkoxy. Preferred alkoxysilanes are 3-isocyanatopropyltriethoxysilane and 3-isocyanatopropyltrimethoxysilane.

Suitable polyisocyanates are the aliphatic systems, known from polyurethane chemistry, such as ethylene diisocyanate, tetramethylene diisocyanate, hexamethylene diisocyanate, dodecamethylene diisocyanate, cyclobutane-1,3-diisocyanate, cyclohexane-1,3-diisocyanate, cyclohexane-1,4-diisocyanate, 1-isocyanato-3,3,5-trimethyl-5-isocyanatomethyl-cyclohexane (isophorone diisocyanate), N-isocyanatohexylaminocarbonyl-N,N'-bis-isocyanatohexyl) urea, 1,1-methylene-bis-(4-isocyanatocyclohexane), 4,4'-diisocyanatodicyclohexylmethane, 2,4,6,-trioxo-1,3,5-tris (6-isocyanatohexyl)hexahydro-1,3,5-triazine or 2,4,6-trioxo-1,3,5-tris(5-isocyanato-1,3,3-trimethylcyclohexylmethyl)hexahydro-1,3,5-triazine.

Preferably, cycloaliphatic or mixed aliphatic-cycloalipathatic polyisocyanates are used for the inventive method. Particularly preferred is 1-isocyanato-3,3,5-trimethyl-5-isocyanatomethyl-cyclohexane (isophorone diisocyanate).

Suitable catalysts for the synthesis of the alkoxysilyl-functionalized polyethers, used pursuant to the invention, are also known from polyurethane chemistry (for example, Ullmann's Encyclopedia of Industrial Chemistry, vol. A21, pp. 665 to 717, VCH Publishers Inc., 1992). These catalysts are, for example, Lewis bases, such as 1,4-diazabicyclo (2.2.2.)octane (DABCO) or 1,8-diazabicyclo(5.4.0)-7-undecene (DBU) or Lewis acids such as dibutyl tin dilaurate (DBTL) or tin dioctoate. The catalyst-free synthesis of the alkylsilyl-functionalized polyethers, used pursuant to the invention, is preferred.

By mixing alkoxysilyl-functionalized polyethers (component A) with water and organic and/or inorganic acids in a ratio by weight of 1:0.1 to 1:40 (component B), elastomeric products are obtained, which can be used in an outstanding manner as impression or doubling compositions in the dental area.

Component A as well as component B may contain further conventional auxiliary materials or additives for formulating pasty products. Auxiliary materials and/or additives are understood to be, for example, diluents, such as aromatic or aliphatic hydrocarbons, alcohols, ethers, polyethers, esters, polyesters, fillers such as quartz powder, cristobalite powder, calcium sulfate, diatomaceous earth, silicates, precipitated or pyrogenic, silica with or without a coated surface, additives, dyes, colors, fragrances, flavorings, emulsifiers and stabilizers.

Preferably, components A and B are offered for use in tubes, tubular bags or double cartridges.

Elastomeric impressions, based on the inventive impression compositions, can be prepared in ways known to those skilled in the art. Components A and B can be mixed by hand or by automatic mixing systems. For the user, the parameters of processing time and setting time are very important parameters of an impression material. It is desirable that, for a practical processing time, which generally falls within the range of a few minutes, a setting time can be adjusted to a value, which is only slightly longer than the processing time. The setting characteristics of elastomeric impression compositions can be quantified, for example, by means of rheometric methods. The amounts of the storage module G' (as a measure of the elastic portion of an impression material) and of the loss module G'' (as a measure of the viscous portion of an impression material) can be determined by measurements by means of oscillation rheometry. Furthermore, the equation, $\tan \delta = (G''/G')$ applies. By observing the course of the curing as a function of the time elapsed since the start of the mixing by means of oscillation rheometry, the times can be determined at which $G'=G''$ or $\delta=45°$ ($t_1$) or $\delta=10°$ ($t_2$); in this connection, $t_1$ can be interpreted as the processing time and $t_2$ as the curing time of the impression material. The ratio $t_2/t_1$ can be regarded as a quantity for characterizing the setting kinetics. The closer this ratio is to 1, the more advantageous is the setting behavior in the direction of "snap-set". For impression compositions based on or alkoxysilyl-functional polyethers corresponding to the state of the art, the $t_2/t_1$ ratio of is found to be of the order of 1.7 to 2.0. On the other hand, in the case of the inventive systems, a ratio of $t_2/t_1$ of 1.2 to 1.3 can be achieved.

It is extremely surprising that the inventive impression compositions are distinguished by setting kinetics, which are significantly more advantageous than those of impression compositions of the state of the art.

EXAMPLES

Example 1
General Method for the Synthesis of Alkoxysilyl-functionalized Polyethers from Polyether Polyols.

A polyether polyol (300 g) is dehydrating for one hour at 10 mbar and 100° C. Subsequently, one mole of isocyanatopropyltriethoxysilane per mole of hydroxy group is added followed by 1 drop of dibutyl tin dilaurate. The mixture is stirred at 100° C. until isocyanate groups can no longer be detected (see Table 1, A1 to A5).

Example 2
Synthesis of Alkoxysilyl-functionalized Polyethers from Polyethers with Terminal Amino Groups
General Method:

A polyether (300 g) with terminal amino groups is dehydrated for one hour at 10 mbar and 100° C. After the polyether has cooled to 60° C., a mixture of isocyanatopropyltrialkoxysilane, isophorone diisocyanate and cyclohexyl isocyanate is added dropwise over a period of 30 minutes, so that the molar ratio of amino groups to isocyanate groups is 1:1. The mixture is stirred at 60° C., until isocyanate groups can no longer be detected (see Table 1, A7 to A11).

Comparison Example

The synthesis of a linear poly(ether-urea) polyaddition product of EP 0 269 819 B1, Example 3, requires two steps and leads to a very viscous end product (see Table 1, V1).

Example 3
Formulation of the Catalyst Component B

| | |
|---|---|
| 32.2% | dihydroxy-polypropylene oxide (MW 2000) |
| 2.8% | paraffin |
| 0.3% | emulsifier |
| 59.2% | quartz powder |
| 3.2% | pyrogenic silica and |
| 2.3% | of a 16 percent aqueous solution of p-toluenesulfonic acid hydrate | are mixed in a mixer in the sequence given to form a homogeneous, pasty composition. The mixing time is 30 minutes at 50 rpm.

Example 4

The polyether with alkoxysilyl terminal groups, which is described in Examples 1 and 2, and commercially obtainable polyethers with terminal alkoxysilyl groups are mixed intensively in a ratio by weight of 1:1 with the catalyst component B. After a few minutes, a product is obtained, which has been cross-linked into an elastic material.

Example 5
Formulation of a Dental Impression Composition:

| | |
|---|---|
| 19.1% | A10 |
| 19.1% | diluent |
| 54.5% | filler (quartz powder) |
| 4.0% | paraffin and |
| 3.8% | polyethylene fibers | are homogenized into a pasty composition in a mixer (component A).

Components A and B are mixed intensively for 30 seconds in a ratio by weight of 1:1.

The physical characterization of the impression composition according to ISO 4823 provides the following results,

| | |
|---|---|
| Viscosity | 153.6 |
| Processing Time (min) | 1.8 |
| Curing Time (min) | 2.4 |
| Curing Time/Processing Time | 1.3 |
| Recovery after Deformation (%) | 97.7 |
| Dimensional Change (%) | 0.45 |
| Shore A Hardness (1 h) | 52 |

Comparison Example

| | |
|---|---|
| 19.1% | V1 |
| 19.1% | diluent |
| 54.5% | filler (quartz powder) |
| 4.0% | paraffin and |
| 3.8% | polyethylene fibers | are homogenized to a pasty composition (component A) in a mixer

Components A and B are mixed intensively for 30 seconds in a ratio by weight of 5:1. Investigations of the setting kinetics and of the physical characterization of the impression composition by the method of ISO 4823 gave the following results:

| | |
|---|---|
| Viscosity (23° C., 3s 1) (Pas) | 275 |
| Processing Time (min) | 2.2 |
| Curing Time (min) | 3.8 |
| Curing Time/Processing Time | 1.7 |
| Recovery after Deformation (%) | 98 |
| Dimensional Change (%) | 0.36 |
| Shore A Hardness (1 h) | 51 |

What is claimed is:

1. A dental impression or doubling composition, comprising

A) alkoxysilyl-functional polyethers with linear or branched main chains with an average molecular weight (Mn) of 800 to 20,000, containing
20 to 95 percent of polyether groups and
0.2 to 25 percent of $SiR^1R^2R^3$ alkoxysilyl groups, in which $R^1$, $R^2$ and $R^3$, independently of one another, are hydrogen, alkyl or alkoxy, and
0 to 10 percent of urea groups;
wherein component A) is free of urethene groups; and B) a mixture, containing water and organic acids, inorganic acids or both in a ratio by weight of 1:0.01 to 1:40.

2. The dental impression or doubling composition of claim 1, wherein component A) has a branched main chain.

3. The dental impression or doubling composition of claim 1, wherein component A) has an average molecular weight (Mn) of 1500 to 15000.

4. The dental impression or doubling composition of claim 1, wherein component A contains 2 to 15% —$SiR^1R^2R^3$ alkoxysilyl groups.

5. The dental impression or doubling composition of claim 1, wherein components A) and B) are offered in tubes, tubular bags or double cartridges.

6. A method for preparing a dental restoration which comprises preparing said dental restoration with a dental impression or doubling composition comprising A) alkoxysilyl-functional polyethers with linear or branched main chains with an average molecular weight (Mn) of 800 to 20,000, containing
20 to 95 percent of polyether groups and
0.2 to 25 percent of $SiR^1R^2R^3$ alkoxysilyl groups, in which $R^1$, $R^2$ and $R^3$, independently of one another, are hydrogen, alkyl or alkoxy, and
0 to 10 percent of urea groups;
wherein component A) is free of urethane groups; and B) a mixture, containing water and organic acids, inorganic acids or both in a ratio by weight of 1:0.01 to 1:40.

* * * * *

UNITED STATES PATENT AND TRADEMARK OFFICE
CERTIFICATE OF CORRECTION

PATENT NO.    : 6,835,760 B2
DATED         : December 28, 2004
INVENTOR(S)   : Schaub et al.

It is certified that error appears in the above-identified patent and that said Letters Patent is hereby corrected as shown below:

<u>Title page,</u>
Item [73], Assignee, "Heraues" should read -- Heraeus --

<u>Column 7,</u>
Line 22, "urethene" should read -- urethane --

Signed and Sealed this

Seventeenth Day of May, 2005

JON W. DUDAS
*Director of the United States Patent and Trademark Office*